US011026621B1

United States Patent
Yu et al.

(10) Patent No.: US 11,026,621 B1
(45) Date of Patent: Jun. 8, 2021

(54) COLLABORATIVE CONCUSSION SENSING SYSTEM FOR BETTER CONCUSSION PREDICTION

(71) Applicants: Maddox J Yu, San Jose, CA (US); Aaliyah J Yu, San Jose, CA (US)

(72) Inventors: Maddox J Yu, San Jose, CA (US); Aaliyah J Yu, San Jose, CA (US)

(73) Assignee: Aegis Of Soteria LLC, San Jose, CA (US)

( * ) Notice: Subject to any disclaimer, the term of this patent is extended or adjusted under 35 U.S.C. 154(b) by 0 days.

(21) Appl. No.: 17/025,907

(22) Filed: Sep. 18, 2020

(51) Int. Cl.
*A61B 5/00* (2006.01)

(52) U.S. Cl.
CPC .......... *A61B 5/4064* (2013.01); *A61B 5/0004* (2013.01); *A61B 5/0022* (2013.01); *A61B 5/6803* (2013.01); *A61B 5/7275* (2013.01); *A61B 2503/10* (2013.01)

(58) Field of Classification Search
CPC ... A61B 5/4064; A61B 5/0004; A61B 5/0022; A61B 5/6803; A61B 5/7275; A61B 2503/10
See application file for complete search history.

(56) References Cited

U.S. PATENT DOCUMENTS

| | | | |
|---|---|---|---|
| 9,024,770 B2 | 5/2015 | Reuben | |
| 9,149,227 B2 * | 10/2015 | Benzel | A61B 5/1114 |
| 9,326,737 B2 * | 5/2016 | Simon | A61B 5/1121 |
| 9,936,756 B1 * | 4/2018 | Yu | G16H 50/30 |
| 10,251,433 B2 * | 4/2019 | Roberts | A41D 1/002 |
| 10,433,033 B2 * | 10/2019 | Touma | H04Q 9/00 |
| 10,520,378 B1 * | 12/2019 | Brown | A61B 5/7267 |
| 10,660,546 B2 * | 5/2020 | Saigh | G16H 20/30 |
| 2011/0184319 A1 | 7/2011 | Mack | |
| 2015/0040685 A1 | 2/2015 | Nicholson | |

(Continued)

Primary Examiner — Jonathan T Kuo

(57) ABSTRACT

A system that uses information from multiple players involved in an impact to improve the measurement of impact g-force by collaborative analysis and hence improve the prediction of the risk of concussion for an athlete, which includes a wearable device with an impact sensor and an application processor, and a smartphone mobile application. The wearable device is mounted to the player's helmet or other locations where the impact force to the head is measured. The wearable device wirelessly communicates with a smartphone, where the measured g-force, including magnitude and direction, from the wearable device, is obtained and an iterative optimization algorithm is run to make the correction and/or optimization of the measurement based on the law of physics. The said iterative optimization algorithm takes into the consideration of the data from all players involved in the impact, and minimize the error based on the law of physics. Potentially a cloud-based data storage system and an algorithm improvement system can be included. The impact force data and all related information can be uploaded from the smartphone to a cloud-based database for storage. An algorithm improvement system will periodically analyze the data in order to build a better collaborative analysis algorithm for optimization. Once a better optimization algorithm is identified, such an algorithm will be sent to or downloaded by the smartphone for better analysis.

2 Claims, 5 Drawing Sheets

(56) References Cited

U.S. PATENT DOCUMENTS

| | | | |
|---|---|---|---|
| 2015/0173669 A1* | 6/2015 | Simon | A61B 5/4076 |
| | | | 600/595 |
| 2015/0226621 A1* | 8/2015 | Zhu | G01L 5/0052 |
| | | | 702/41 |
| 2016/0292509 A1 | 10/2016 | Kaps et al. | |
| 2016/0331319 A1 | 11/2016 | Kozloski | |
| 2017/0127736 A1* | 5/2017 | Roberts | A41D 31/285 |
| 2017/0272842 A1* | 9/2017 | Touma | A63B 43/00 |
| 2017/0318360 A1 | 11/2017 | Tran et al. | |
| 2019/0192053 A1* | 6/2019 | Saigh | A61B 5/02055 |

\* cited by examiner

US 11,026,621 B1

COLLABORATIVE CONCUSSION SENSING SYSTEM FOR BETTER CONCUSSION PREDICTION

BACKGROUND OF THE INVENTION

1. Field of the Invention

The present invention relates generally to a system and method to assess the potential risk to brain damage by measuring the impact force on multiple users under impact and using a collaborative method to improve the accuracy of the measurement and hence the quality of predicting the potential risk of concussion.

2. Description of the Background Art

Concussions due to sports activities, especially in American football, become a larger and larger concern for athletes, coaches, and family members. Historically, athletes are checked by medical personnel on the sideline by examining whether athletes have displayed any symptoms such as dizziness and confusion. Recently, various electronic devices have been proposed and manufactured in attempts to provide a better prediction of potential risk for concussion. However, those systems fall short in various categories.

A typical type of such electronic device is usually mounted on the athlete's helmet, measures the impact g-force, and uses such measurement to predict the likelihood of a concussion. However, due to an extremely short period of the impact (which is usually in the order of milliseconds) and an extremely large g-force (which is usually between 100 g and 300 g), existing sensing hardware usually has a large variation in reading due to technical limitation which leads to an unreliable prediction for concussions. Such inaccuracy becomes a major barrier for players, coaches, and medical personals in an attempt to adopt such a system in a real-life environment. Furthermore, researches have shown that the direction of the impact relative to the front of the brain is a critical factor in predicting the concussion, but currently available sensors are not able to provide acceptable measurement accuracy of direction of impact.

What is needed is a system and method that can improve the accuracy of impact force measurement in order to reliably monitor the impact and to predict the likelihood of a concussion. Such a system and method needs to overcome the technical limitation associated with such an extreme operating condition.

SUMMARY

This invention takes advantage of the fact that an impact usually happens between two or multiple players in sports activities and uses the collative information from multiple players involved in any given impact to improve the accuracy of the measurement.

The inventive system includes a wearable device for each player with an impact sensor and an application processor, a smartphone mobile application with collaborative analysis software, and an optional cloud-based data storage system. The wearable devices are mounted to the players' helmet or other locations where the impact force to the head can be measured, and the measurement data is sent wirelessly to a smartphone on the sideline. When an impact happens, the smartphone recognizes spikes of g-force measurement from multiple players' sensors and runs collaborative analysis across those data to obtain a more accurate g-force measurement.

The physics principle of such collaborative analysis is the conservation of momentum in elastic collisions. The collaborative analysis software on the smartphone can identify which players are involved in the impact by identifying the spike of g-force measurement happening at the same time, combine such data with other pre-registered information from players (such as weight), and based on the law of physics solve multi-dimensional equations or use other algorithms to make corrections on the impact g-force measurement in both magnitude and direction. This optimized reading is then used for concussion prediction.

Optionally, the impact force data can be uploaded from a smartphone to a cloud-based database to further tune the collaborative analysis algorithm. Once a better algorithm is identified, it can be downloaded to the smartphone for future collaborative analysis.

Furthermore, such collaborative analysis may take into consideration of other measurements or information. Specifically, the location of each player and their speed can be measured by a separate optical or electrical system, and such data can be fed into the collaborative analysis software to increase the accuracy of the correction of the impact g-force measurement.

The use of the same reference label in different drawings indicates the same or like components.

DETAILED DESCRIPTION

In the present disclosure, numerous specific details are provided, such as examples of apparatus, components, and methods, to provide a thorough understanding of embodiments of the invention. Persons of ordinary skill in the art will recognize, however, that the invention can be practiced without one or more of the specific details. In other instances, well-known details are not shown or described to avoid obscuring aspects of the invention.

Figure 1:
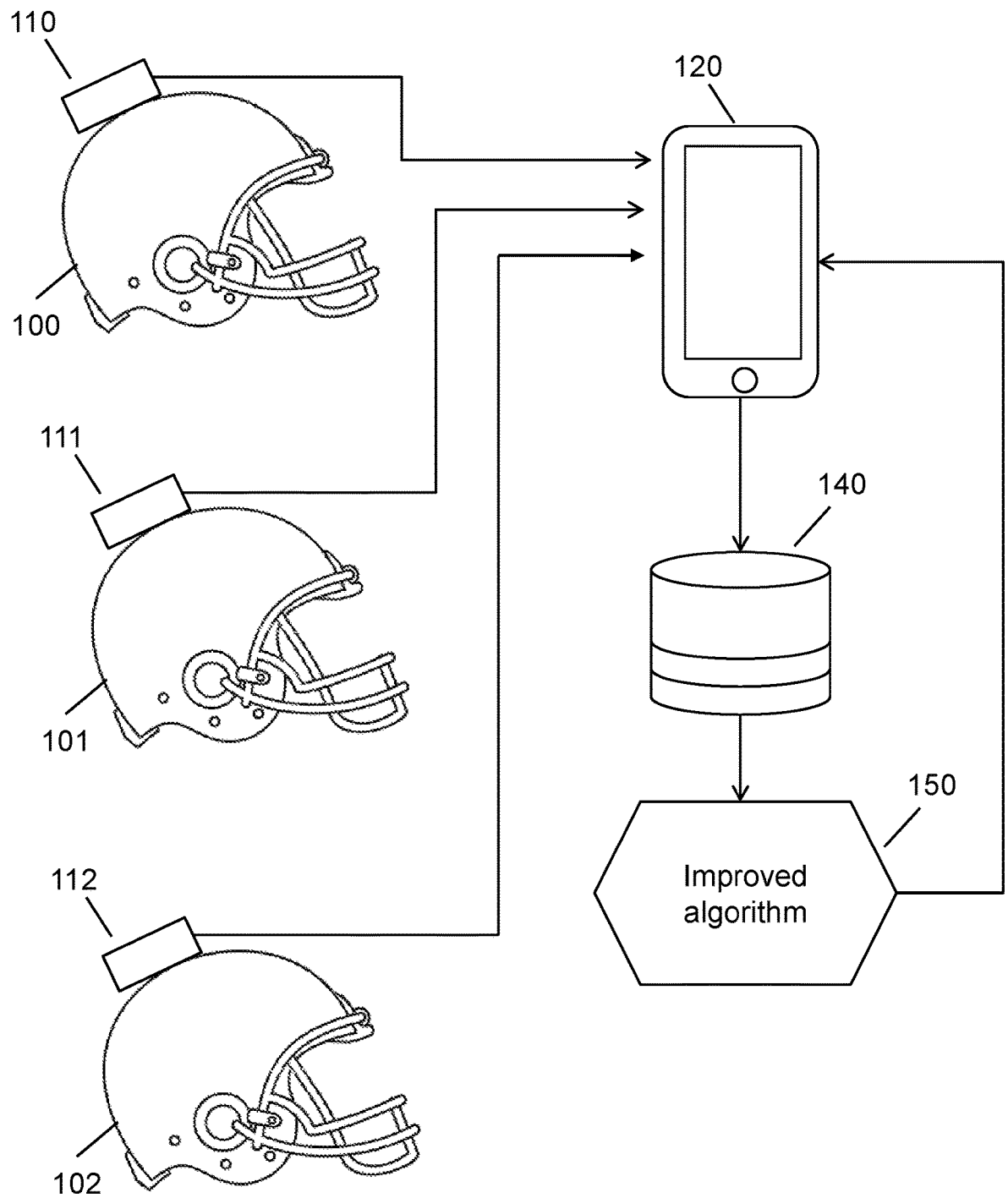
FIG. 1 is a schematic diagram of the system according to the present invention.
Figure 2:
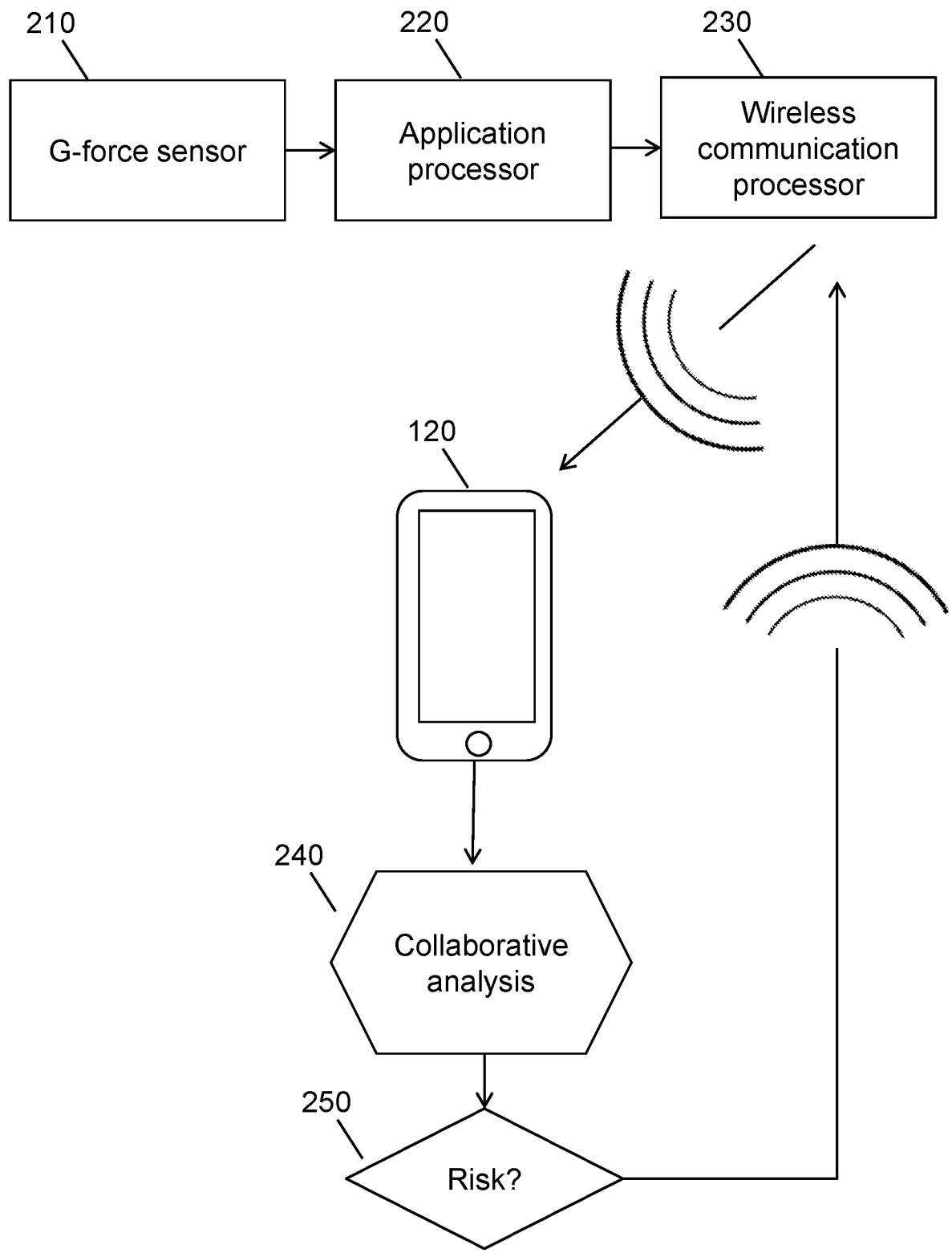
FIG. 2 schematically shows the major components of the wearable device and the information communication path between components of the wearable device and a smartphone.
Figure 4:
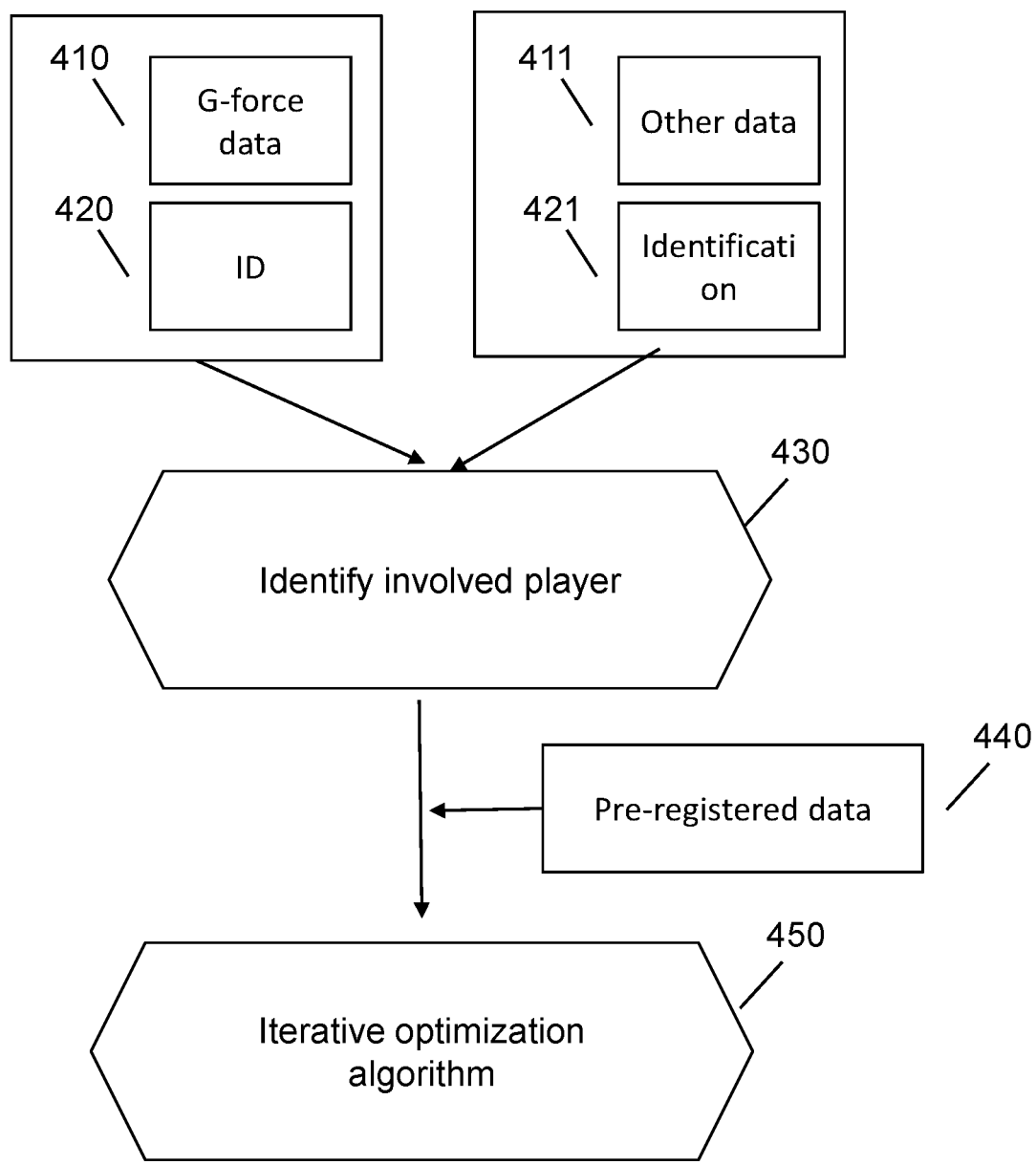
FIG. 4 is a flowchart of collaborative analysis using all available data.
Figure 5:
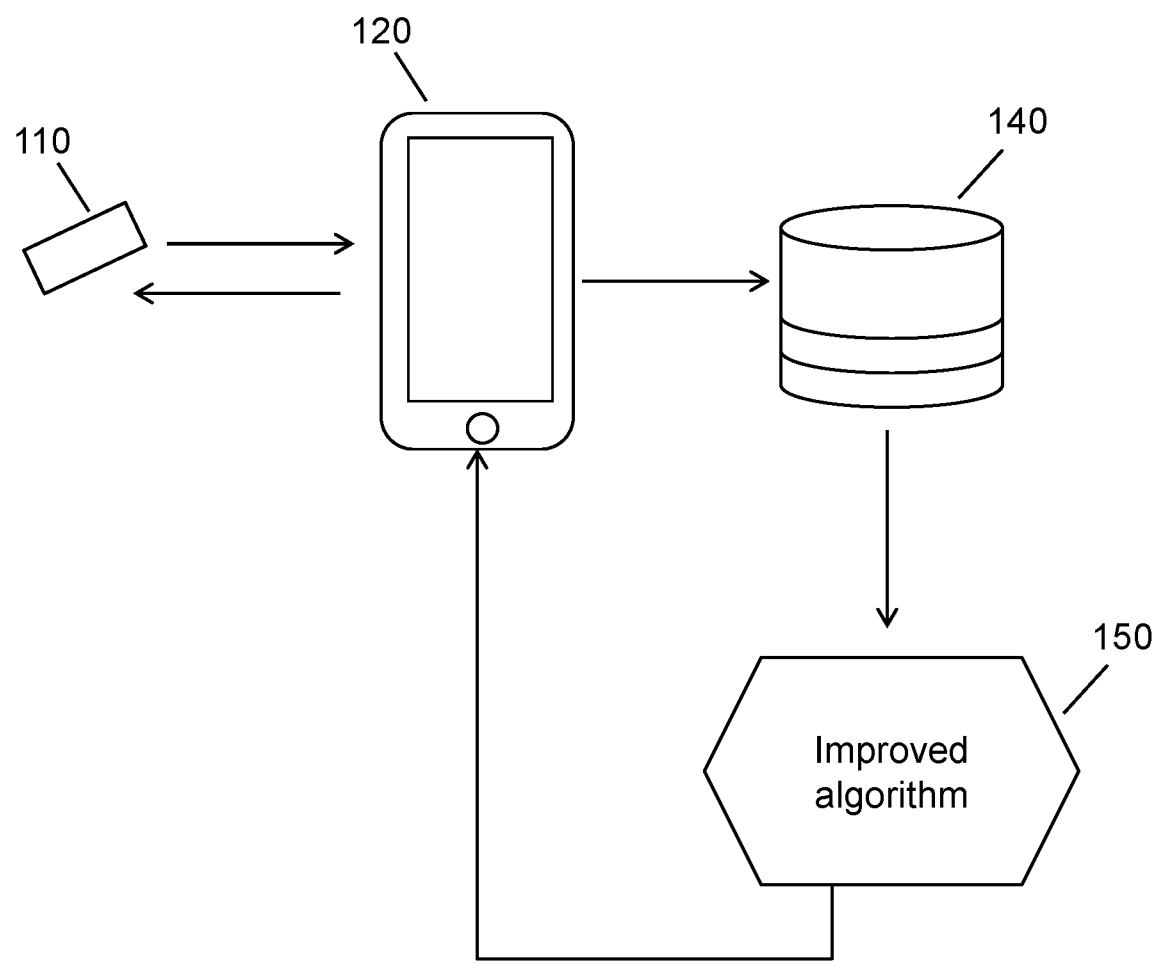
FIG. 5 is a flowchart of the information flow path between the smartphone and the cloud-based data storage system, including the algorithm improvement system.

FIG. 1 shows a flow diagram schematically illustrating the operation of the system. The wearable devices such as 110, 111, 112 are mounted to the players' helmets such as 100, 101, 102, or other locations where the impact force to the head can be measured. When a strong impact is detected (which is illustrated in FIG. 2 and will be further described below), the wearable devices such as 110, 111, 112 send the impact force measurement data, athlete's information (such as ID), and other related information to a smartphones 120 that is wirelessly connected to those wearable devices through Bluetooth or other wireless communication protocol. The smartphone runs collaborative analysis (which is illustrated in FIG. 4 and will be further described below) to make a correction or other optimization of the impact g-force measurement, which could be further used for concussion prediction. Furthermore, the information can be uploaded through a wireless internet connection to a cloud-based storage system 140 (such as Amazon Web Service Cloud). With sufficient data volume, analysis can be performed on the data (which is illustrated in FIG. 5 and will be further described below) and a better collaborative analysis algorithm 150 could be discovered to make better correction or optimization. Such improved algorithm 150 is then sent through the internet to the smartphone 120 for future usage.

More detail about the operation between the wearable devices and the smartphone is illustrated in FIG. 2. The wearable device comprises a g-force sensor 210 that may detect acceleration up to 400 g in three-dimensional space and may have a measurement frequency up to milliseconds. The g-force measured is read by an application processor 220. If the impact g-force is large enough (as determined by certain threshold and/or algorithm by 220), all related information will be sent from the wearable device to the smartphone 120 through the wireless communication processor 230 inside the wearable device. The connected smartphone 120 will receive related information and run collaborative analysis 240 to make correction or optimization of the measured impact g-force, which is then used for the prediction of the potential risk of concussion 250. If such risk is identified, the smartphone could send a related warning to the identified player's wearable device through the same wireless protocol above.

Figure 3:
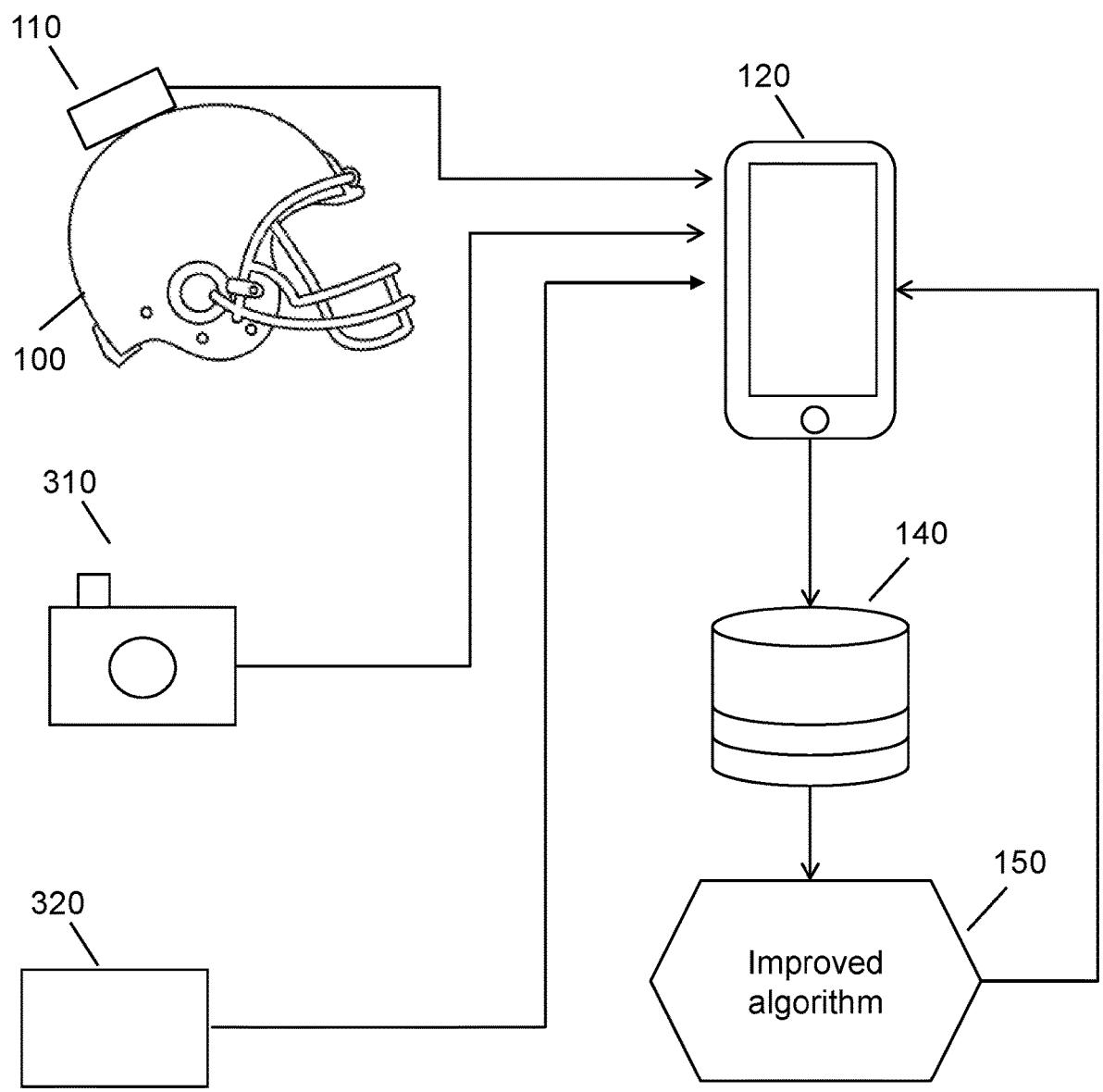
FIG. 3 schematically shows other information that could be incorporated into the collaborative analysis to improve the correction of g-force impact force measurement.

The collaborative analysis could use other additional information to make better correction or optimization of the measured impact g-force, as illustrated in FIG. 3. One example of such information is the location and speed of each player by a camera 310 mounted above the field of play. Many systems and software are available to convert camera images into location, speed, and other information for each player. The smartphone 120 can communicate with such systems to obtain such data as input for collaborative analysis. Many other location and speed acquisition systems are possible, as illustrated in FIG. 3 as component 320.

FIG. 4 is an illustration of how collaborative analysis works. The information sent to the smartphone includes the g-force data 410 as measured by wearable device 110. Given that each wearable device 110 contains a unique ID that is specific to each player, this ID information 420 is also sent to the smartphone. Other data 411 and associated identification 421, such as information collected by 310, could also be sent to the smartphone. When such data are received, the first step is to identify which players are involved in the impact and which players are not. This is done by examining which players' g-force data show a spike over time. If other data 411 is available, such timestamp from the spike of g-force data is used to allocation other data 411 that happens at the same time, and any location information from other data 411 can be used to further verify whether the identified players are physically located at the same place on the field (which is required if a collision happens). After the involved players are identified, their pre-registered data 440 can be retrieved from a database on the smartphone or the cloud, such as a player's weight information. All those data are then fed into an iterative optimization algorithm 450 to find the correct and/or optimal impact g-force measurement for each player. In general, an iterative method is a mathematical procedure that uses an initial guess (which is the actual g-force data measured) to generate a sequence of improving approximate solutions that maintain conservation of momentum (and/or other law of physics) during the impact, in which the n-th approximation is derived from the previous ones. Unlike any other products and/or devices described in the Background Art, instead of looking into only one player's measurement, this innovative system takes into consideration of all involved players' g-force magnitude and direction (plus other data if available). If there is any measurement error from any device, the conservation of momentum will not be held. In such a case, a small change (correction) of the measured data can be made to get the result closer to the conservation of momentum (and/or other law of physics). A specific implementation of an iterative method, including the termination criteria, can be implemented using various algorithms, such as stationary iterative methods and the more general Krylov subspace methods. The iterative method is called convergent if the error from the conservation of momentum (and/or other law of physics) is smaller than a pre-defined value.

Optionally, such related information can be sent to a cloud-based storage system 140, as illustrated in FIG. 5. When concussion-related information is received from a wearable device 110, the smartphone 120 can upload such information to the cloud-based storage system 140 using standard industry protocols and procedure. When sufficient data has been collected (usually at the range of hundreds of data points) in the cloud-based storage system 140, a better collaborative analysis algorithm can be explored, as illustrated in FIG. 5. This may involve the practice of various algorithms such as stationary iterative methods vs the Krylov subspace methods, or various data filtering methods, or a combination of both. Once an improved collaborative analysis algorithm 150 is identified, such an algorithm will be sent to or downloaded by the corresponding smartphone 120, and such an algorithm will be used for future collaborative analysis.

While specific embodiments of the present invention have been provided, it is to be understood that these embodiments are for illustration purposes and not limiting. Many additional embodiments will be apparent to persons of ordinary skill in the art reading this disclosure.

What is claimed is:

1. A system that uses information from multiple players involved in an impact to improve the measurement accuracy of impact g-force and hence improve the prediction accuracy of the risk of concussion for an athlete, comprising:

wearable devices operatively worn on the head of multiple athletes, each of which contains an impact force measurement sensor to measure the impact g-force, an application processor to process the impact g-force, and a wireless communication processor to send information to a smartphone;

a smartphone mobile application that connects wirelessly to said wearable devices, wherein the measured impact g-force, including magnitude and direction, from the wearable devices, are obtained wirelessly, and an iterative optimization algorithm is run to make a correction and/or optimization of the measurement accuracy based on conservation of momentum which takes into consideration the impact g-force from all players involved in the impact and minimizes measurement error.

2. The system of claim 1 wherein:

the smartphone mobile application is configured to collect location and speed data from all players involved in the impact and to feed the location and speed data into the iterative optimization algorithm in order to improve the measurement accuracy; and to pre-register weight information of each player who is involved in the impact and to feed the weight information into the iterative optimization algorithm in order to improve the measurement accuracy.

\* \* \* \* \*